United States Patent
Adachi

(10) Patent No.: US 10,607,809 B2
(45) Date of Patent: Mar. 31, 2020

(54) RADIATION IMAGING APPARATUS

(71) Applicant: SHIMADZU CORPORATION, Nakagyo-Ku, Kyoto-Shi, Kyoto (JP)

(72) Inventor: Kazunori Adachi, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 99 days.

(21) Appl. No.: 15/980,988

(22) Filed: May 16, 2018

(65) Prior Publication Data

US 2018/0337018 A1 Nov. 22, 2018

(30) Foreign Application Priority Data

May 17, 2017 (JP) .................................. 2017-097894

(51) Int. Cl.

| | |
|---|---|
| *A61B 6/04* | (2006.01) |
| *H01J 37/20* | (2006.01) |
| *H04N 1/00* | (2006.01) |
| *G03B 27/72* | (2006.01) |
| *G06F 3/0481* | (2013.01) |
| *G06F 3/0488* | (2013.01) |
| *G03B 42/02* | (2006.01) |
| *A61B 6/00* | (2006.01) |

(52) U.S. Cl.
CPC ................ *H01J 37/20* (2013.01); *A61B 6/04* (2013.01); *A61B 6/0407* (2013.01); *G03B 27/725* (2013.01); *G03B 42/025* (2013.01); *G06F 3/0488* (2013.01); *G06F 3/04812* (2013.01); *H04N 1/00411* (2013.01); *A61B 6/4441* (2013.01); *A61B 6/467* (2013.01)

(58) Field of Classification Search
CPC ....... A61B 6/0407; A61B 6/4441; A61B 6/03; A61B 6/0421; A61B 6/04; A61B 6/467; G06F 3/04845; G06F 3/04886
See application file for complete search history.

(56) References Cited

U.S. PATENT DOCUMENTS

2005/0017871 A1* 1/2005 Kagermeier ............. A61B 6/04
340/12.55
2017/0215827 A1* 8/2017 Johnson ............... A61B 6/4441

FOREIGN PATENT DOCUMENTS

JP 2006-109990 11/2007

\* cited by examiner

*Primary Examiner* — David P Porta
*Assistant Examiner* — Fani Boosalis
(74) *Attorney, Agent, or Firm* — Andrew F. Young, Esq.; Lackenbach Siegel, LLP

(57) ABSTRACT

An X-ray imaging apparatus comprises a first operation unit 31 and a second operation unit 41 that execute an input operation relative to an X-ray image displayed on a display element. The first operation unit comprises a touch panel and the second operation unit comprises a lever. A mounted first operation unit can change an angle relative to a rail installed relative to a table. The second operation unit is attachable to both the rail and the table, and first operation unit is and detachable therefrom for convenience.

3 Claims, 8 Drawing Sheets

RADIATION IMAGING APPARATUS

CROSS REFERENCE TO RELATED APPLICATIONS

This application relates to, and claims priority from JP 2017-097894 filed May 17, 2017, the entire contents of which are incorporated herein by reference.

FIGURE SELECTED FOR PUBLICATION

FIG. 3

BACKGROUND OF THE INVENTION

Field of the Invention

The present invention relates to a radiation imaging apparatus such as an X-ray imaging apparatus to execute an X-ray imaging for a subject.

Description of the Related Art

Such X-ray imaging apparatus in the art comprises a table that is tiltable and movable while a subject is loaded, an X-ray irradiation element that irradiates an X-ray to the subject loaded on the table, an X-ray detection element that acquires an X-ray image by detecting the X-ray that the X-ray irradiation element irradiates and transmits through the irradiated subject, and a display element that displays the X-ray image acquired by the X-ray detection element.

The X-ray irradiation element and the X-ray detection element are supported by e.g., C-arm and so forth and move in a unified manner, so that an X-ray imaging can be executed from a variety of directions.

Such X-ray imaging apparatus further comprises a moving element that moves the table horizontally and tilts the table and in addition, is operative to move the C-arm, and an operation unit that is operative to execute a variety of operations relative to the X-ray image to be displayed on the display element. The driving element and operation unit respectively comprise a lever-type input mechanism. In addition, the operation unit comprises a touch panel consisting of a liquid crystal display and so forth, i.e., both display function and input function (refer to Patent Document 1).

RELATED PRIOR ART DOCUMENTS

Patent Document 1

Japanese Patent JP 2006-109990 A

ASPECTS AND SUMMARY OF THE INVENTION

Objects to be Solved

Relative to such X-ray imaging apparatus, the operation unit is preferably in-place in the location where it facilitates the medical doctor or a medical technician to operate. Accordingly, the operation unit is installed to the arbitrary location on the rail attached to the side of the table. In case, the table tilts, so that the operator can hardly see such touch panel angle-wise. Therefore, the operation unit is mounted in the state in which the mounting angle thereof is changeable. Accordingly, regardless of the angle of the table, the angle of the operation panel can be adjusted to facilitate to see the image on the touch panel.

However, when the angle of the operation unit varies, the mounting-angle of the lever-type input mechanism changes at the same time, so that it is problematic that the lever operation of the lever-type input mechanism is too hard to be operative.

The purpose of the present invention is to solve the above objects and to provide an X-ray imaging apparatus that does not impair the operability of the lever-type input mechanism even when the mounting angle varies along with tilting the table.

Means for Solving the Problem

According to an aspect of the present invention, a radiation imaging apparatus comprises a table that tilts and moves while a subject is loaded, a radiation irradiation element that irradiates a radiation to a subject that is loaded on the table, a radiation detection element that detects the radiation that the radiation irradiation element irradiates and acquires a radiation image thereby, a display element that displays the radiation image that the radiation detection element acquires, and the radiation imaging apparatus further comprises a first operation unit having a display function and an input function, a mounting mechanism that mounts the first operation unit so that the mounting angle thereof is changeable relative to a rail installed to a side of the table, and a second operation unit, which has a lever-type input element, a mounting element relative to the rail installed to the side of the table and a mounting element relative to the first operation unit, is attachable to the rail and the first operation unit and detachable therefrom.

According to another aspect of the present invention, the above first operation unit further comprises a touch panel having a display function and an input function.

According to another aspect of the present invention, the above first operation unit and the above second element execute inputting the operation relative to the radiation image to be displayed on the display element.

Effect of the Invention

According to another aspect of the present invention, the second operation unit having the lever-type input mechanism is attachable to both first operation unit having the display function and input function and the rail and detachable from both, and as a result, even when the mounting angle of the operation unit varies, the second operation unit is mounted to the rail according to necessity, so that the lever-type input mechanism is operative with preventing the operability thereof from impairment. In addition, the first operation unit having the display function and input function and the second operation unit having the lever-type input mechanism are mounted in a unified manner relative to the table or even individually, so that the mounting aspect of the first and second operation units can be modified in accordance with the aspect of the radiation imaging.

According to another aspect of the present invention, the above touch panel can be mounted to provide better visibility (visual recognition).

According to another aspect of the present invention, the mounting facilitates to execute the operation relative to the radiation image to be displayed on the display element.

The above and other aspects, features and advantages of the present invention will become apparent from the fol-

DETAILED DESCRIPTION OF THE PREFERRED EMBODIMENTS

Figure 1:
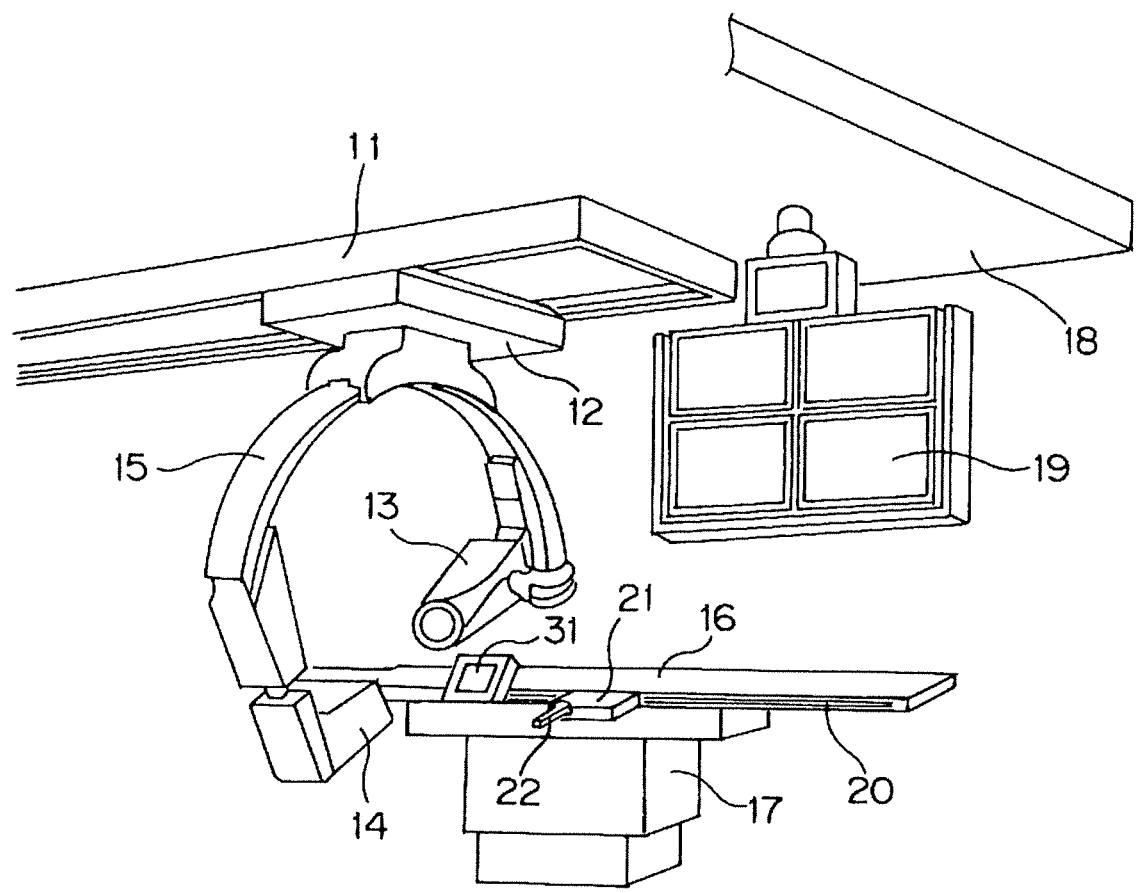
FIG. 1 is a perspective view illustrating an X-ray imaging apparatus.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

As used herein, an 'operation element' or 'radiation element' or 'operation unit' or other device, structure or feature etc. will be understood to be well understood by those of skill in the art, which is understood to be a very high skill in the art with a great deal of pre-existing technical, engineering, computer, and scientific knowledge including each of Applicant's other published patent applications for similar Radiation Imaging devices, to include the features and structures necessary to function as described without having to identify every input/output element, display, lever, memory element, storage feature, trigger, rail, switch, wire, plug, processing unit, display screen, etc. etc. and/or wherein any computer code resident in a memory will physically cause the processor to change and to read-in data via an input device (e.g., including via a radiation imaging apparatus, touch screen, toggle-lever etc.), process data within the processor or processors (plural) and output processed data via an output output device such as a viewing image screen or display which is changed to show the output image generated.

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents (resistors, capacitors, transistors, heat sinks, links, switches etc.) noted herein and structures that accomplish the functions without restrictive language or label requirements since those of skill in the art are well versed in related radiation fluoroscopy imaging apparatus and devices, computer and operational controls and technologies of radiographic devices and all their sub components, including various circuits and combinations of circuits without departing from the scope and spirit of the present invention.

Although only a few embodiments have been disclosed in detail, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The inventor sets forth Embodiments of the present invention based on the following FIGs. FIG. 1 is a perspective view illustrating an X-ray imaging apparatus as a radiation imaging apparatus according to the aspect of the present invention. In addition, referring to FIG. 1, only the first operation unit 31 out of the first operation unit 31 and the second operation unit 41 is mounted to the table 16.

Such X-ray imaging apparatus carries out an X-ray fluoroscopy or an X-ray imaging (hereafter, collectively X-ray imaging) comprises an X-ray irradiation element 13 that irradiates an X-ray to a subject on the table 16 supported by the supporting element 17 and an X-ray detection element 14 having an X-ray detector such as FPD (flat panel detectors) or II (image intensifier) and so forth that detects the X-ray transmitting through the subject. The X-ray irradiation element 13 and the X-ray detection element 14 are supported by C-arm 15 having the shape approximately as letter C. Such C-arm 15 is supported by a carriage 12 that shifts in one direction by that the guide element 11 fixed on the ceiling guide.

A rail 20 is installed on the side of the table 16. The rail 20 comprises the shifting element 21 having a lever 22 that is operative to shift horizontally and tilt, and in addition, to shift the C-arm 15 and the first operation unit 31 having a touch panel 32 (referring to FIG. 3) that is operative to display and input to execute inputting the operation relative to the X-ray image displayed on the display element 19. The table 16 is movable horizontally and tiltable according to the action of supporting element 17. In addition, referring to FIG. 1, the rail 20 shown only one side of the table 16, but each rail is respectively on both sides of the table 16.

In addition, such X-ray imaging apparatus comprises a display element 19 that displays the X-ray image acquired by the X-ray detection element 14. Such display element 19 comprises a plurality of monitors and hangs from the ceiling 18.

Figure 2:
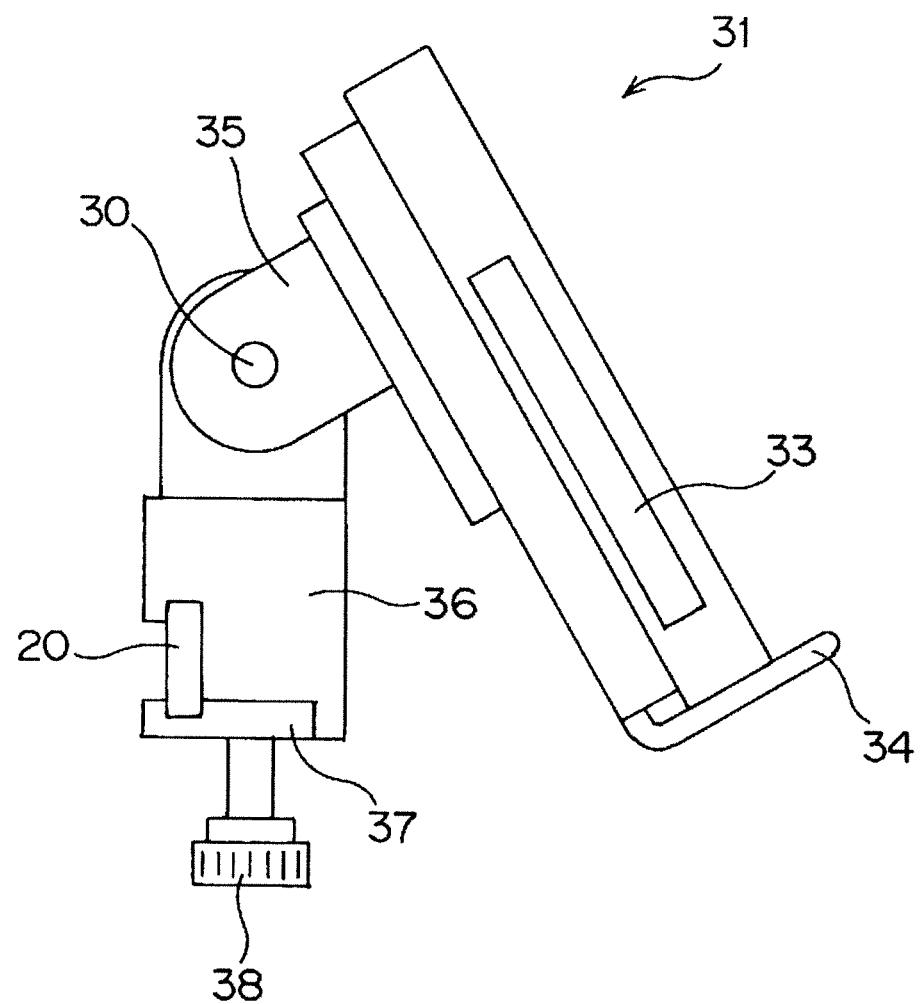
FIG. 2 is the side view illustrating the status in which the first operation unit 31 is mounted to the rail 20.
Figure 3:
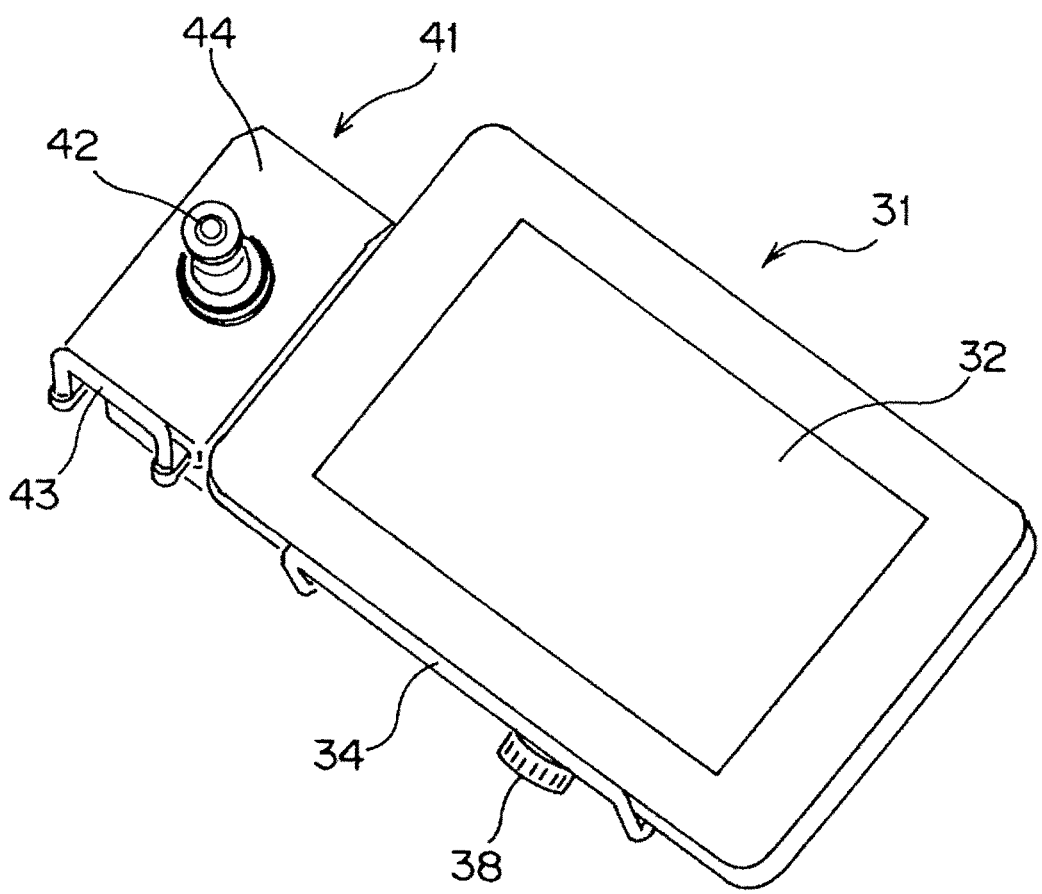
FIG. 3 is a perspective view illustrating the first operation unit 31 and the second operation unit 41 together.

FIG. 2 is a side view illustrating the state in which the first operation unit 31 is mounted to the rail 20. In addition, FIG. 3 is a perspective view illustrating the first operation unit 31 and the second operation unit 41 together.

Such first operation unit 31 having the touch panel 32 that is operative to display and input to execute inputting the operation relative to the X-ray image displayed on the display element 19. Such touch panel 32 comprises a supporting element 35 on the backside thereof. The supporting element 35 is oscillable at the center of the axis 30 relative to the mounting element 36. In addition, the rail 20 is in-place between the mounting element 36 and the mounting auxiliary board 37 and the mounting element 36 and the mounting auxiliary board 37 sandwich and hold the rail 20 using a function of the screw 38. The mounting angle of the touch panel 32 relative to the rail 20 is adjustable by the operation of the second operation unit 41 installed to the bottom-side of the touch panel 32. Referring to FIG. 2, the first operation unit 31 comprises a first connection element 33 having the shape connectible with a second connection element 45 of the second operation unit 41, set forth later.

Figure 4:
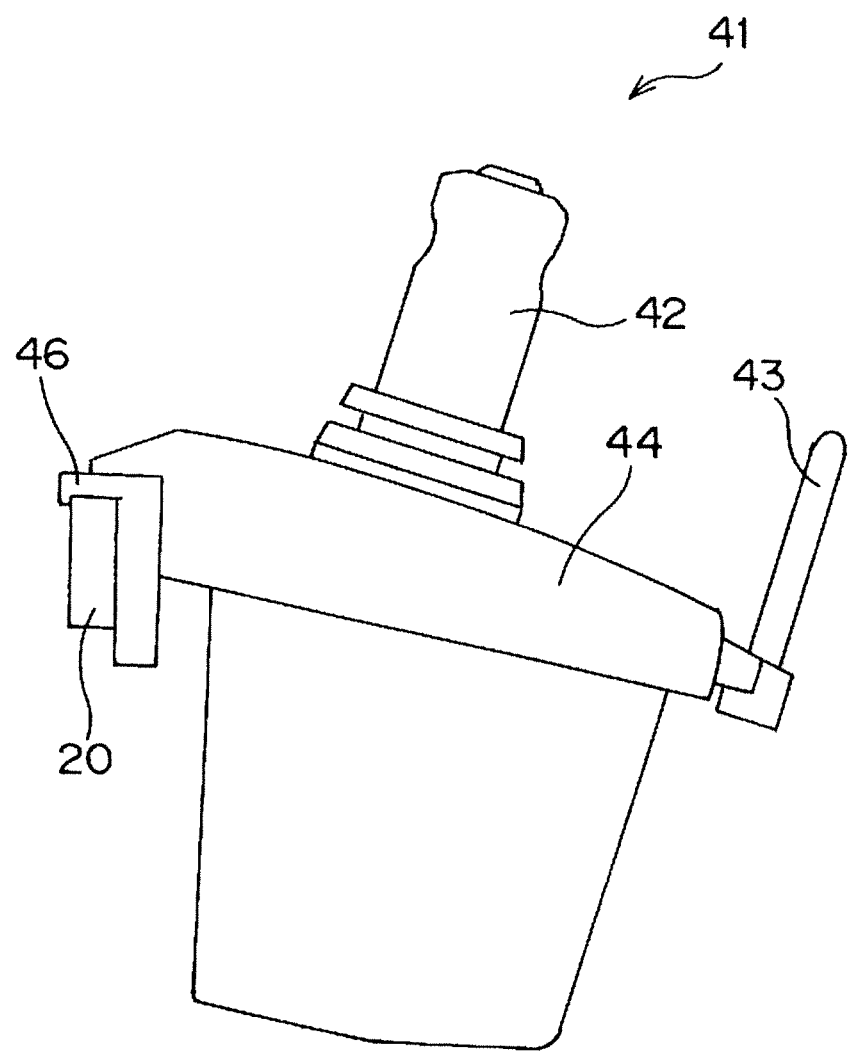
FIG. 4 is the side view illustrating the status in which the second operation unit 41 is mounted to the rail 20.
Figure 5:
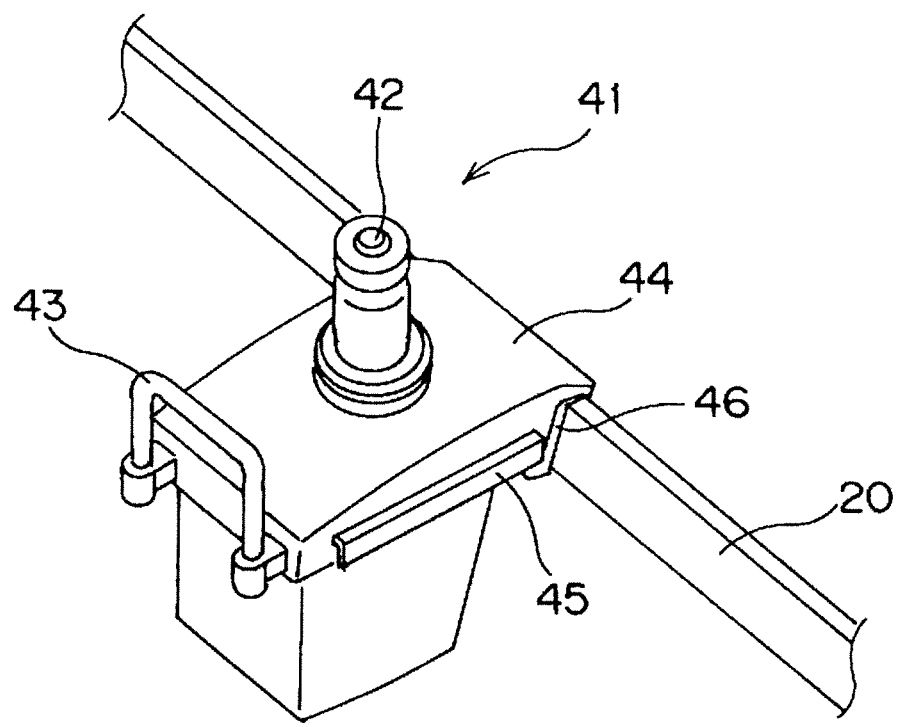
FIG. 5 is the perspective view illustrating the status in which the second operation unit 41 is mounted to the rail 20.

FIG. 4 is a side view illustrating the state in which the second operation unit 41 is mounted to the rail 20. FIG. 5 is a side view illustrating the state in which the second operation unit 41 is mounted to the rail 20. In addition, FIG. 6 is a schematic view illustrating the connection state between the first connection unit 33 in the first operation unit 31 and the second connection unit 45 in the second operation unit 41.

Such second operation unit 41 comprises the lever 42 that is feasible to change the tilting direction relative to the main body 44 to execute the input operation relative to X-ray image displayed on the display element 19 The second operation unit 41 comprises the mounting element 46 that locks and mounts the second operation unit 41 with the rail 20. The second operation unit 41 is mounted to the rail 20 by that the operator locks the mounting element 46 with the rail 20 while the operator is supporting the operation unit 43. Referring to FIG. 5, 6, set forth above, the second operation unit 1 comprises a second connection element 45, having the shape connectible with a first connection element 33 of the first operation unit 31, at the side thereof.

Figure 6:
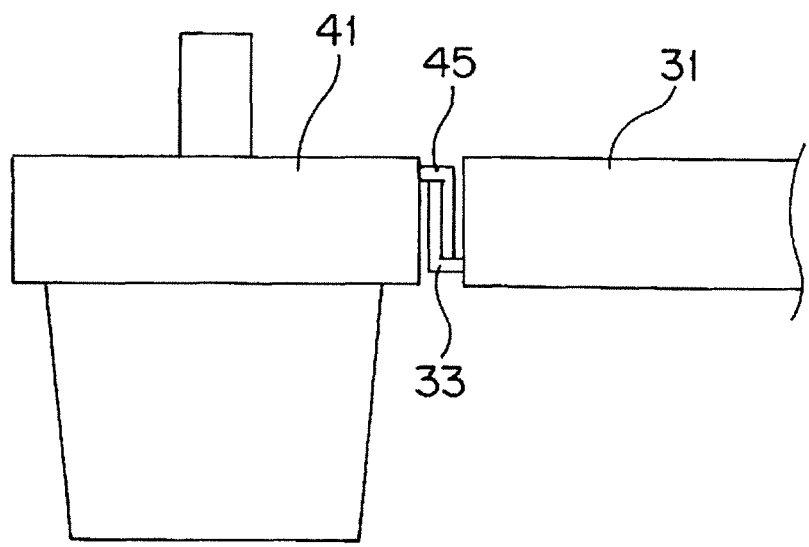
FIG. 6 is a schematic view illustrating the connection state between the first connection unit 33 in the first operation unit 31 and the second connection unit 45 in the second operation unit 41.

Referring to FIG. 6, with respect to the first connection element 33 of the first operation unit 31 and the second connection element 45 of the second operation unit 41, the second connection element 45 having the cross section of which shape is an approximately upside-down letter L is connected with the first connection element 33 having the cross section of which shape is an approximately letter L, so that the second operation unit 41 can be fixed to the first operation unit 31.

According to the X-ray imaging apparatus having such structures, the first operation unit 31 and the second operation unit 41 execute the input operation relative to the X-ray image displayed on the display element 19. For example, relative to the first operation unit 31, the operator executes the operation, such as an image processing of the X-ray image that is displayed on the display element 19. In addition, relative to the second operation unit 41, the medical doctor executes the operation including such as feeding and selection of the image displayed on the display element 19 or a decision of the point location in the image displayed on the display element 19 and so forth.

At this time, relative to the X-ray imaging apparatus according to the aspect of the present invention, the second operation unit 41 can also be mounted to the first operation unit 31 that is mounted on the rail 20 or can be mounted directly to the rail 20. Therefore, when it is desirable that both first operation unit 31 and second operation unit 41 run at the same time, referring to FIG. 3, the second operation unit 41 is just mounted to the first operation unit 31 that is mounted to the rail 20. In addition, when the first operation unit 31 is in-place in the angle at which the image on the touch panel 32 is easily and visually recognizable corresponding to the angle of the table 16 and the input operation using the lever 42 relative to the second operation unit 41 is difficult, the second operation unit 41 can be directly mounted to the rail 20.

In addition, in such cases when the technician operates the first operation unit 31 and the medical doctor operates the second operation unit 41 operates, the first operation unit 31 and the second operation unit 41 can be individually in-place where the operators can easily operate.

In addition, according to the aspect of the Embodiment set forth above, the first connection element 33 and the second connection element 45, of which the cross sections are the approximately letter L shape, are used to mount the second operation unit 41 to the first operation unit 31. However, the structure by which the second operation unit 41 is mounted to the first operation unit 31 is not limited to such structure.

Figure 7:
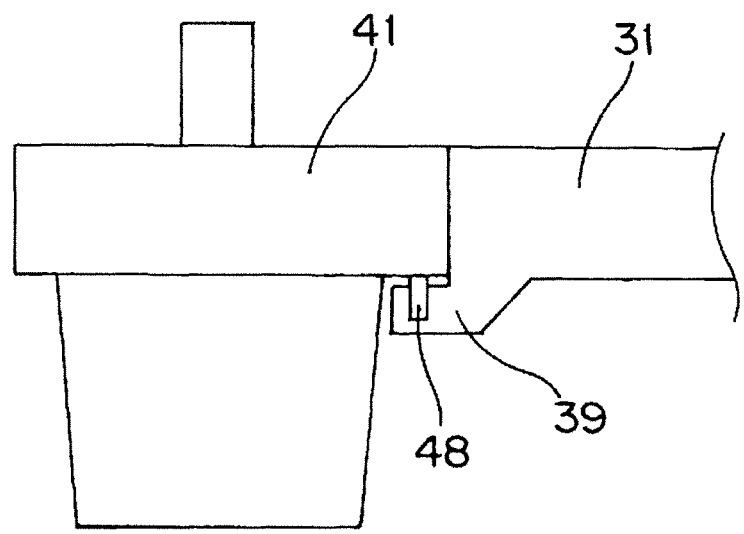
FIG. 7 is a schematic view illustrating the connection state between the first connection unit 33 in the first operation unit 31 and the second connection unit 45 in the second operation unit 41 according to another Embodiment.

FIG. 7 is a schematic view illustrating the connection state between the first connection unit 33 of the first operation unit 31 and the second connection unit 45 of the second operation unit 41 according to an aspect of another Embodiment.

According to the aspect of the Embodiment referring to FIG. 7, a protrusion 39 having the convex element is attached relative to the first operation unit 31 and a pin 48 that can be inserted into the concave element formed to the protrusion 39 relative to the first operation unit 31 is attached relative to the second operation unit 41. According to the aspect of the Embodiment set forth above, the pin 48 relative to the second operation unit 41 is inserted into the concave element formed to the protrusion 39 of the first operation unit 31, so that the second operation unit 41 can be mounted to the first operation unit 31.

Figure 8:
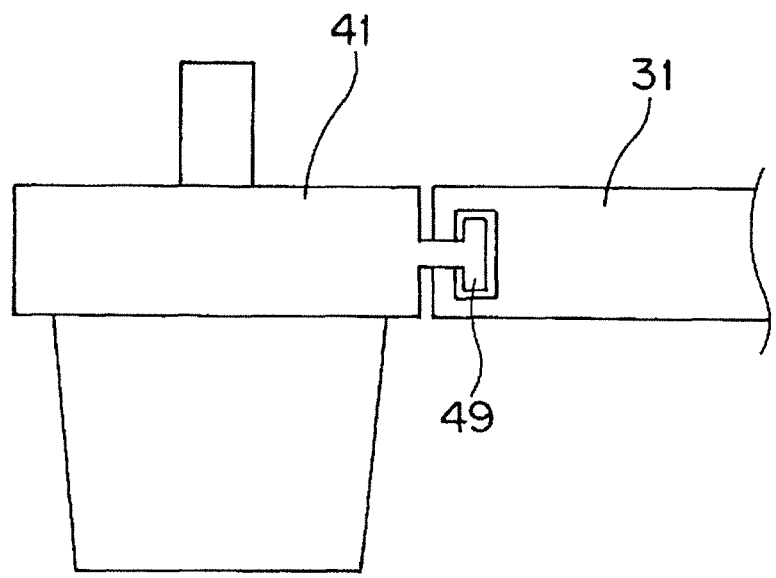
FIG. 8 is a schematic view illustrating the connection state between the first connection unit 33 in the first operation unit 31 and the second connection unit 45 in the second operation unit 41 according to further another Embodiment.

FIG. 8 is a schematic view illustrating the connection state between the first connection unit 33 of the first operation unit 31 and the second connection unit 45 of the second operation unit 41 according to the aspect of further another Embodiment.

According to the aspect of the Embodiment referring to FIG. 8, a hollow portion is formed relative to the first operation unit 31 and a convex element 49, which is additionally installed relative to the second operation element 41, can be inserted into the hollow portion that is formed relative to the first operation unit 31. According to the aspect of the Embodiment set forth above, the second operation unit 41 is slid from the lateral direction and the convex element 49 of the second operation unit 41 is inserted into the hollow portion formed to the first operation unit 31, so that the second operation unit 41 can be mounted to the first operation unit 31.

REFERENCE OF SIGNS

13 X-ray irradiation element
14 X-ray detection element
15 C-arm
16 Table
17 Supporting element
19 Display element
20 Rail
21 Shifting element
30 Axis
31 First operation unit
32 Touch panel
33 First connection element
35 Supporting element
36 Mounting element
37 Mounting auxiliary board
38 Screw
39 Protrusion
41 Second operation unit
42 Lever
45 Second connection element
46 Mounting element
48 Pin
49 Convex element Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A radiation imaging apparatus, comprising:
    a table that tilts while a subject is loaded;
    a radiation irradiation element that irradiates a radiation to said subject that is loaded on said table;
    a radiation detection element that detects the radiation that said radiation irradiation element irradiates and transmits through said subject and acquires a radiation image thereby;
    a display element that displays said radiation image that said radiation detection element acquires;
    a first operation unit that has a display function and an input function;
    a first mounting mechanism that mounts said first operation unit so that a mounting angle is changeable relative to a rail installed at a side of said table;
    a second mounting mechanism that has a lever as an input mechanism and is mounted to said rail installed to said side of said table, the first mounting mechanism and second mounting mechanism being securable to one another; and
    a second operation unit that is attachable to and detachable from said first operation unit.

2. The radiation imaging apparatus, according to claim 1, wherein:
    said first operation unit, further comprising:
        a touch panel that has a display function and an input function.

3. The radiation imaging apparatus, according to claim 1, wherein:
    said first operation unit and said second operation unit are operative to execute an input relative to the radiation image displayed on said display element.

* * * * *